United States Patent [19]

Forsyth et al.

[11] Patent Number: 5,027,804
[45] Date of Patent: Jul. 2, 1991

[54] BANDAGES

[75] Inventors: Christine H. Forsyth; Richard H. Pearce, both of Hull, United Kingdom

[73] Assignee: Smith & Nephew plc, United Kingdom

[21] Appl. No.: 424,261

[22] PCT Filed: Apr. 8, 1988

[86] PCT No.: PCT/GB88/00278
§ 371 Date: Oct. 11, 1989
§ 102(e) Date: Oct. 11, 1989

[87] PCT Pub. No.: WO88/07847
PCT Pub. Date: Oct. 20, 1988

[30] Foreign Application Priority Data

Apr. 11, 1987 [GB] United Kingdom ................ 8708721

[51] Int. Cl.$^5$ ................................................ A61F 5/04
[52] U.S. Cl. ........................................ 128/90; 128/85; 128/89
[58] Field of Search ................. 128/90, 82, 85, 89; 428/253, 254; 66/197, 198, 202

[56] References Cited

U.S. PATENT DOCUMENTS

| 3,885,015 | 6/1975 | Ono et al. | 264/282 |
| 4,668,563 | 5/1987 | Buese et al. | 428/259 |
| 4,793,330 | 12/1988 | Honeycutt et al. | 428/254 |

Primary Examiner—Randall L. Green
Assistant Examiner—R. Clarke
Attorney, Agent, or Firm—Rosenman & Colin

[57] ABSTRACT

A substrate suitable for use in a water hardenable orthopaedic splinting bandage is formed from a knitted fabric in which the yarn running along the length of the substrate is from a heat shrinkable yarn so that after heat treatment the substrate is stretchable in the lengthwise direction. The heat shrinkable yarn is suitably a polyester or polyamide and the non-heat shrinkable yarn is suitably a different polyester or polypropylene. Preferably the substrate has a lengthwise extension of not less than 5% and not more than 30%. A water hardenable orthopaedic bandage in which the substrate is impregnated with a water curable resin particularly an isocyanate-containing resin is also described.

15 Claims, No Drawings

BANDAGES

The present invention relates to water hardenable orthopaedic splinting bandages comprising a fabric substrate impregnated with a moisture- or water-curable resin and in particular a resin containing isocyanate groups. More particularly the present invention relates to an orthopaedic bandage comprising a fabric substrate which is stretchable in the lengthwise direction and to the substrate itself.

Conventionally orthopaedic splinting bandages for use in the treatment of bone fractures or other conditions requiring immobilization of part of the body are formed from a substrate impregnated with a substance which hardens to a rigid structure after wrapping the strip around the body. Traditionally plaster of Paris was used but more recently certain plastics and reinforced plastics have gained acceptance as replacements for plaster of Paris. Such new bandages are lighter, waterproof and permeable to X-rays. One advantage which may be achieved with the newer form of cast is that the final cast may be strong without requiring as many layers of material making up the cast as with plaster of Paris and so facilitates the evaporation of moisture from the skin underlying the cast. One way in which strength is added to such casts is to use a substrate which not only acts as a carrier for the resin but also provides strength to the final cured bandage, for example U.S. Pat. Nos. 3,421,501 and 3,881,473 describe, in a preferred bandage, an ultraviolet curing resin on a glass fibre fabric. Other glass fibre fabrics are disclosed in U.S. Pat. Nos. 3,882,857, 3,773,688 and 3,787,272. More recently International Application No. 81/00671 has described, in a preferred form, a water curable polyurethane resin impregnated on a glass fibre fabric. U.S. Pat. No. 4,323,061 describes a substrate formed from glass fibres interwoven with a yarn which is a combination of glass fibre and a second fibre. One disadvantage of glass fibre casts is that they may become brittle and break down during wear and hence need to be replaced. This disadvantage may be mitigated by using a substrate which with a suitable resin provides a cast which is more durable than a cast formed using a glass fibre substrate. Aptly these substrates do not contain glass fibres. However, heretofore such substrates lack the conformability found with glass fibre substrates.

Surprisingly we have found that by using a fabric which does not contain glass fibres and which is stretchable in the lengthwise direction to form the substrate a bandage is achieved which has improved conformability compared to existing fabric substrates and which does not show a loss of strength compared to a glass fibre substrate. The substrate will have a degree of stretch in the lengthwise direction provided by using a heat shrinkable fibre in the yarn used in the lengthwise direction of the bandage.

In one aspect therefore the present invention provides a warp knitted fabric substrate suitable for use in a water hardenable orthopaedic splinting bandage characterised in that yarn forming the warp running along the length of the substrate is heat shrinkable and that the substrate has been heat treated whereby it is stretchable in the lengthwise direction.

In a second aspect the present invention provides a water hardenable orthopaedic splinting bandage comprising a warp knitted fabric substrate impregnated with a water curable resin characterised in that yarn forming the warp running along the length of the substrate is heat shrinkable and that the substrate has been heat treated whereby it is stretchable in the lengthwise direction.

The substrate therefore suitably contains at least two different types of yarn. The yarn forming the stitching along the length of the substrate containing a heat shrinkable component and optionally a non-shrinkable component whereby after heat treatment the yarn shrinks and may be stretched to its preshrunk length under tension. This yarn provides a degree of stretch in the length direction along the substrate which improves the conformability of the bandage on application. The yarn which forms the yarn across the width of the fabric is non-glass fibre and aptly does not shrink under the influence of heat.

Suitable heat shrinkable components of the yarn include polyester yarns and polyamide yarns such as multifilament yarns formed from a polyamide known as nylon 6,6. A suitable yarn comprises a mixture of polypropylene filaments and polyamide filaments. Aptly when both are present the ratio of non-shrinkable to shrinkable components in the yarn may be from 2:1 to 1:2 and is preferably 1:1.

Suitable yarns which form the remainder of the fabric are aptly non-heat shrinkable and include such yarns as polyester and polypropylene. Suitable polyester yarns are polyethylene terephthalate yarns. A preferred yarn is formed from filaments of polypropylene.

Suitably the substrate will have a thickness of from 0.015 to 0.050 inches, more suitably will be 0.018 to 0.040 inches thick preferably 0.020 to 0.035 inches thick, for example 0.033 inches.

The substrate will be in the form of a flexible fabric which has been knitted. Suitable knit-types for the substrate are described in for example International Patent Application No. 81/00671 now U.S. Pat. No. 4,609,578. Suitable fabrics may be employed as a Raschel knit, a crochet knit or a tricot knit. A preferred substrate will be in the form of a warp knitted fabric having a chain stitch along its length. The knit is suitably of a type which prevents formation of frayed ends when the substrate is cut.

The substrate will be extensible in both lengthwise direction and optionally also in the widthwise direction so as to provide good conformability and lamination particularly when wrapped around parts of the body such as the elbow or heel. Suitably the widthwise extension will be from 50 to 100%, more suitably 60 to 95% and preferably 75 to 95% for example 80%. Suitably the lengthwise extension will be greater than 5% but less than 30% more suitably 8 to 20% for example 10, 12 and 16%. The lengthwise extension is provided by heat treatment of the substrate to cause shrinkage of the heat shrinkable yarns lying in the lengthwise direction of the substrate.

The degree of heat treatment determines the amount by which the heat shrinkable yarn shrinks and hence the lengthwise extension given to the substrate. Suitable methods of heat treatment include exposing the substrate to steam, hot water, heating in an oven or passing slowly through a heated oven or tunnel. For example steam may cause shrinkage of approximately 12% in a polyester substrate and passage of a polypropylenepolyamide substrate through an oven at 80° C. for 9 minutes may cause shrinkage of about 7 to 9%.

The lengthwise extension may be measured by any convenient method such as using an Instron Tensile Testing Machine. A 10 cm length of substrate may be clamped in the jaws of the machine and the jaws separated at constant speed. A conventional stress strain curve for the substrate may be recorded. The extension at a given load and the load required to give a given extension can be calculated from the curve for the substrate under test.

Suitably the substrate may be a mesh, that is it should have openings through it to enable the curing agent to penetrate into the roll and expose all parts of the resin. The mesh may be defined by counting the number of repeating patterns of the knit on a square inch of the fabric. This may be accomplished by taking a photograph of a section of the substrate when relaxed at known magnification and counting the recurring units across and along the section for a distance equivalent to an inch in each direction and multiplying the two figures together. Suitably the fabric will have a mesh of from about 120 to 250 per sq inch more suitably from 150 to 220 per sq inch and preferably 160 to 200 per sq inch for example 170, 180 190, or 200 per sq inch. Suitably the knitted substrate may have a weight per unit area of from 50 to 500 gm$^{-2}$, more suitably may be 100 to 300 gm$^{-2}$ and preferably a weight of 150 to 250$^{-2}$.

The resins used in the casting material of the invention may be any curable resin which will satisfy the functional requirements of an orthopaedic cast. The resins are those cured with water or moisture and include the resins described in U.S. Pat. Nos. 4,667,661, 4,574,793, 4,502,479, 4,433,680, 4,427,002, 4,411,262, 3,932,526, 3,908,644, 3,630,194, in German Offenlegungsschrift No. 2651089, and in European Patent Application Nos. 35517, 57988, 86621 and 94222.

Aptly the resin used to coat the fibre substrate may be a cold water curable isocyanate terminated polyurethane prepolymer system. Among suitable polyurethane prepolymer systems are those identified in U.S. Pat. Nos. 4,411,262, 4,427,002, 4,433,680 and 4,574,793. Particularly preferred are those systems disclosed and claimed in U.S. Pat. Nos. 4,427,002 and 4,574,793 the disclosures of which are incorporated herein by cross-reference.

Suitably the bandage will be formed by coating or impregnating the substrate with the resin in the manner described in those patents, particularly in U.S. Pat. No. 4,427,002.

Suitably the weight of resin on the substrate is from 150 to 500 gm$^{-2}$, more suitably a weight of 200 to 450 gm$^{-2}$ and preferably between 250 to 300 gm$^{-2}$. The wight of resin may be chosen so that suitably 40 to 60% of the total weight of the bandage is resin and more suitably 50 to 55% of the total weight. Thus if the fabric weight is 250 gm$^{-2}$ and the resin coating is 55-60% of the bandage then the weight of resin taken is 305-375 g.

The formed bandages may be packaged by heat sealing in waterproof pouches such as those formed from metal foil polyethylene laminates or polyethylene pouches.

In use the bandages may be brought into contact with water and wrapped around the injured part of the body. The setting bandage has a working time which is sufficient to allow the bandage to be positioned on the limb and a set time which is the time taken for the cast to become rigid. Apt working times are 1 to 6 minutes and apt set times are 5 to 30 minutes.

The cast incorporating the substrate of the invention is readily removable by conventional means such as by cutting with a conventional circular saw. Large casts may be removed using a single cut along the length of the cast which is not always achievable with fibre glass substrate casts.

The build-up of strength in the cast was assessed by wrapping the resin-coated substrate round a former to make a cylinder. The former is removed and the cylinder wall clamped in an Instron Tensile Testing Machine so as to measure diametral compression and extension forces. The machine is adapted so that the moving clamp would oscillate between positions 2.5 mm from the rest position. The force required to deform the cast as it set over a period of time is measured. The results were recorded on a chart recorder. A bandage formed according to Example 2 was tested in comparison with a conventional glass fibre based bandage using cylinders formed of 5 layers of bandage. The bandage according to the invention was comparable in strength to the glass fibre both on initial setting and after 24 hours.

|  | Rigidity (kg/cm width) Time after initiation of set | | |
| --- | --- | --- | --- |
|  | 15 mins | 30 mins | 24 hr |
| Bandage of Example 2 | 2.6 | 3.4 | 4.7 |
| Glass fibre-based bandage | 2.1 | 2.65 | 4.5 |

In one favoured embodiment the present invention provides a water hardenable orthopaedic splinting bandage comprising a substrate coated with a water curable resin which substrate comprises a warp knitted fabric in which the yarn running along the length of the substrate includes a heat shrinkable polyester yarn and the remainder of the fabric comprises a non-heat-shrinkable polyester yarn and the substrate has an extension in the lengthwise direction of 5 to 30%.

In particular preferred embodiment the present invention provides a conformable water-hardenable orthopaedic splinting bandage comprising a substrate coated with a water curable resin which substrate comprises a warp knitted fabric in which the yarn running along the length of the substrate comprises heat shrinkable polyamide filaments and non-heat shrinkable polypropylene filaments and the remainder of the fabric comprises a non-heat shrinkable polypropylene yarn and the substrate has an extension of between 5% and 30%.

EXAMPLE 1

Preparation of Substrate

A substrate is prepared by knitting together a heat shrinkable polyester yarn and a non-heat shrinkable polyester yarn. The knit-type is a Raschel knit in which the heat shrinkable yarns form the warp and the non-heat shrinkable fibres form the weft. The substrate is knitted as a long strip for example 3.6 m or 2.0 m with a width of 10 cm or 7.5 cm.

The knitted fabric has an extension in the widthwise direction of 80% and after heat shrinking of the warp fibres by means of steam, a lengthwise extension of 12%. The knitted fabric has a thickness of 0.033 inch and a mesh size of 180 per sq inch.

EXAMPLE 2

A substrate is prepared in a similar manner to Example 1 except that that weft is prepared from polypropylene yarn and the heat shrinkable yarn comprised 50% polypropylene and 50% polyamide.

EXAMPLE 3

Preparation of Bandages

A viscous prepolymer comprising a purified polyethylene glycol isocyanate terminated prepolymer prepared in the same manner as that described in Example 22 of European Patent Application No. 57988.

A slurry is prepared by mixing a solution of the prepolymer in dry methylene chloride with potassium carbonate, alumina, Sylosiv A3 and Desmodur M44.

A slurry is coated by means of a doctor blade onto a 10 cm wide strip of a warp knit substrate comprising a polyester weft fibre and a heat shrinkable polyester warp fibre. The solvent is then removed. The fabric is heat treated to cause the fibres in the length direction to shrink by 17% approx so that the substrate may be stretched by up to 17% when subjected to tension. The coating is formed at a weight per unit area of 150 g/m². The bandage strip is cut into 1 metre lengths and spooled onto rolls. The bandage rolls are then heat sealed into pouches of low density polyethylene.

A bandage is made into a cast by dipping the bandage roll in water and wrapping around a body member.

EXAMPLE 4

A water curable polyurethane resin system comprising a polyurethane prepolymer described in U.S. Pat. No. 4,574,793 as prepolymer A and containing methane sulphonic acid as stabiliser and bis(2,6 dimethylmorpholino)diethyl ether as catalyst is coated onto a polyester fabric substrate using the process described in U.S. Pat. No. 4,427,002. The polyester fabric has a heat shrunk polyamide yarn in the lengthwise direction. The polyamide yarn is shrunk by means of heat by 12% approximately so that the bandage may be stretched up to 12% when subjected to tension.

The bandage strip is cut into 3 metre lengths and spooled onto rolls. The bandage rolls are then placed in pouches which are heat sealed to prevent exposure of the contents to moisture.

EXAMPLE 5

A bandage is prepared in a similar manner to that described in Example 2 except that the heat shrinkable yarn in the substrate is a 50% polypropylene: 50% polyamide mixture.

EXAMPLE 6

A bandage was prepared in a similar manner to that described in Example 3 except that the non-shrinkable yarn present in the substrate was polypropylene.

We claim:

1. A warp knitted fabric substrate suitable for use in a water hardenable orthopaedic splinting bandage comprising a yarn forming the wale running along the length of the substrate, said yarn being heat shrinkable and the substrate being heat treated whereby it is stretchable in the lengthwise direction.

2. A substrate according to claim 1 in which the heat shrinkable yarn is a heat shrinkable polyester yarn.

3. A substrate according to claim 1 in which the heat shrinkable yarn is a heat shrinkable polyamide yarn.

4. A substrate according to claims 1 in which the knitted fabric contains non-heat shrinkable yarn which comprises polyester or polypropylene.

5. A substrate according to claim 2 in which the knitted fabric contains as weft a non-heat shrinkable polyester yarn and as warp running along the length of the substrate a heat shrinkable polyester yarn.

6. A substrate according to claim 1 in which the yarn running along the length of the substrate comprises non-heat shrinkable and heat shrinkable filaments wherein the weight ratio of non-heat shrinkable to heat shrinkable filaments is from 2:1 to 1:2.

7. A substrate according to claim 6 in which the heat shrinkable filament is heat shrinkable polyamide yarn and the non-heat shrinkable filament is non-heat shrinkable polypropylene.

8. A substrate according to claim 1 which has a lengthwise extension of not less than 5% and not more than 30%.

9. A substrate according to claim 1 in which the knitted fabric is in the form of a Raschel knit.

10. A water-hardenable orthopaedic splinting bandage comprising a substrate impregnated with a water curable resin in which the substrate comprises a warp knitted fabric comprising a yarn forming the wale running along the length of the substrate, said yarn being heat shrinkable and the substrate being heat treated whereby it is stretchable in the lengthwise direction.

11. A splinting bandage according to claim 10 in which the resin is a water curable isocyanate-terminated prepolymer.

12. A splinting bandage according to claim 10 in which the substrate has a lengthwise extension of not less than 5% and not more than 30%.

13. A splinting bandage according to claim 10 in which the resin on the substrate is present at a weight per unit area of 200 to 450 gm$^{-2}$.

14. A splinting bandage according to claim 10 in which the substrate comprises a warp knitted fabric in which the yarn running along the length of the substrate includes a heat shrinkable polyester yarn and the remainder of the fabric comprises a non-heat shrinkable polyester yarn and the substrate has an extension in the lengthwise direction of between 5 to 30%.

15. A splinting bandage according to claim 10 in which the substrate comprises a warp knitted fabric in which the yarn running along the length of the substrate comprises heat shrinkable polyamide filaments and non-heat shrinkable polypropylene filaments and the remainder of the fabric comprises a non-heat shrinkable polypropylene yarn and the substrate has an extension of between 5% and 30%.

* * * * *